United States Patent [19]
Li

[11] 4,096,237
[45] Jun. 20, 1978

[54] IMMUNOASSAY FOR β-ENDORPHIN

[75] Inventor: Choh Hao Li, Berkeley, Calif.

[73] Assignee: Hoffmann-La Roche Inc., Nutley, N.J.

[21] Appl. No.: 777,262

[22] Filed: Mar. 14, 1977

[51] Int. Cl.$^2$ .................. A61K 43/00; G01N 33/16
[52] U.S. Cl. ............................. 424/1; 260/112 R; 424/12
[58] Field of Search .................. 424/1, 12; 23/230 B; 260/112 R

[56] References Cited
PUBLICATIONS

Guillemin et al, Chemical Abstracts, vol. 84, No. 23, Jun. 7, 1976, p. 134, abstract No. 160803b.

*Primary Examiner*—Benjamin R. Padgett
*Assistant Examiner*—Christine M. Nucker
*Attorney, Agent, or Firm*—Samuel L. Welt; George M. Gould

[57] ABSTRACT

A sensitive radioimmunoassay for β-endorphin (β-EP) is disclosed. It appears that the antigenic determinant resides in residues 6-15 of this molecule.

12 Claims, No Drawings

IMMUNOASSAY FOR β-ENDORPHIN

DESCRIPTION OF THE INVENTION

The present invention rleates to a radioimmunoassay for the recently discovered potent opiate agonist and analgesic agent β-endorphin.

β-endorphin has been isolated in a highly purified state from pituitary glands of camel (Li and Chung, Proc. Natl. Acad. Sci. U.S.A., 73, 1145 (1976), pig (Bradbury et al. Nature (London), 260, 165 (1976) and man (Li et al., Biochem. Biophys. Res. Commun., 72, 1542 (1976)). The respective structures are as follows:

Camel β-endorphin ($β_c$-endorphin or $β_c$-EP)=H-Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-His-Lys-Lys-Gly-Gln-OH Human β-endorphin ($β_h$-endorphin or $β_h$-EP)=H-Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-Tyr-Lys-Lys-Gly-Glu-OH The structures have been confirmed by solid phase synthesis (Li et al., Biochem. Biophys. Res. Commun., 71, 19 (1976)); see also U.S. Pat. application Ser. No. 667,747, filed Mar. 17, 1976, now U.S. Pat. No. 4,038,222.

The assay of the present invention utilizes a β-endorphin specific antibody. Such antibody is readily elicited using an antigen obtained by covalent conjugation of βendorphin with an immunogenic carrier material. Suitable procedures for such conjugation are well known in the art. A preferred procedure is disclosed in the paper of Goodfriend et al., Science 144, 1344 (1964).

Examples of immunogenic carrier materials useful in the practice of this invention are known per se. They include mammalian serum proteins such as gamma globulins or albumins derived from human, goat, rabbit, horse, guinea pig or other mammals. Alternatively it is possible to utilize synthetic polypeptides such as polylysine as the immunogenic carrier material.

The resulting antigen is then injected into a suitable mammalian host until the desired β-endorphin specific antibodies are elicited in the animal's blood. Suitable mammalian host for antibody production are knwon in the art and include rabbit, guinea pig, goat, sheep and the like. The animals are bled periodically and the antibody titer is followed until desired levels are observed. Antiserum to β-endorphin can then be collected by bleeding the host animal.

As the tracer compound in the subject assay, one can employ a radiolabelled β-endorphin. Suitable radiolabelled β-endorphins include $^{14}C$, $^3H$ and $^{125}I$ labelled β-endorphin. A preferred radiolabelled β-endorphin for the purposes of this invention is $^{125}I$-β-endorphin which can be obtained by treating purified β-endorphin by procedures known in the art such as the lactoperoxidase method described by Aubert et al., Acta Endocrinol. 77, 460 (1974).

$^{14}C$-β-endorphin can be readily prepared by introducing one or more appropriate $^{14}C$-labelled amino acids selected from the amino acids occurring in the β-endorphin sequence into the synthesis of this compound.

A convenient method for preparing $^3H$-β-endorphin is to substitute 3,4-dehydroproline for proline in the synthesis and then treating the resulting analog with tritium over a palladium oxide catalyst.

The readioimmunoassay is carried out by incubating is bubbered solution the labelled β-endorphin tracer compound, the sample containing the unknown concentration of β-endorphin and the antiserum for about 16 to 20 hours. The free and bound β-endorphin are separated using techniques known in the art such as by the addition of activated charcoal and dextran. Either the supernatant or the precipitate can be counted. The concentration of β-endorphin in the sample can then be determined by comparing the counts observed with a standard curve derived by treating fixed amounts of tracer compound and antisera with various known concentrations of β-endorphin and plotting the counts observed against such concentrations.

Experiments have been carried out with the instant assay comparing the reactivity of various β-endorphin related peptides. Such studies show that human and camel β-endorphins gave a completely parallel and almost identical inhibition curve. A related fragment $β_c$-EP-(6–31) also exhibited a parallel inhibition curve but had 40% immunoreactivity as compared to the full sequence camel-β-endorphin ($β_c$-EP). On the other hand the synthetic fragment $β_h$-EP-(1–5)-(16–31) showed very weak cross reaction. Moreover, $β_c$-EP-(20–31) and $β_c$-EP (1–5) (met-enkephalin) did not shown any cross-reactivity. Finally, it was found that the pro-hormone human β-lipotropin ($β_h$-LPH), which contains the complete amino acid sequence of $β_h$-EP, exhibited only 10% immunoreactivity with the $β_h$-EP anti-sera.

Based on the foregoing it appears that the antigenic determinant of β-EP is located in residues 6–15. Since both camel and human β-EP have identical sequence in this portion of their structures it is evident that anti-sera derived from antigens containing either compound or any fragment incorporating antigenic determinant. Moreover, the assay will be useful to detect all analogs and fragments of β-endorphin which contain the β-endorphin (6–15) residue sequence.

While the assay of the present invention has been described utilizing radiolabeled β-endorphin or a fragment thereof containing the (6–15) residue sequence it is within the skill of the art to also employ β-endorphin or a fragment thereof containing the (6–15) residue sequence labeled with any other unique and detectable label such as for example an electron spin resonance group. Examples of the use of various electron spin resonance labeled molecules in bioassays are to be found in U.S. Pat. Nos. 3,453,288, 3,481,952 and 3,507,876. Other suitable labels include chromophores, fluorophors, enzymes, red blood cells, latex particles, etc.

The present invention is further illustrated by the examples which follow:

EXAMPLE 1

$β_h$-EP was conjugated with human γ-globulin by the procedure of Goodfriend et al., cited above. Rabbits and guinea pigs were immunized with the conjugate according to the pro-buffer of Vaitukaitis et al., J. Clin. Endocrinol. Metabol. 33,988 (1971). The antigen was dissolved in 0.01 M phosphate buffer of pH 7.5 and emulsified with complete Freund's adjuvant. The emulsion was injected at multiple sites on the backs of animal, which had also received 0.5 ml of Petrussis vaccine two days prior to the administration of the anigen. Each animal received a total of one mg of antigen over a period of five weeks, after which they were test bled, by ear vein for rabbits and cardiac puncture for guinea pigs.

Of the three rabbits and five guinea pigs immunized, one rabbit and two guinea pigs responded with production of antibodies. However it was noted that the guinea pig antiserum was generally of higher titer than the rabbit antiserum. Antiserum from guinea pig No. 2 was used at a final dilution of 1:3000.

The serum was checked for the presence of antibodies by testing its ability to bind $^{125}$I-labeled $\beta_h$-EP which was prepared by the lactoperoxidase method as described by Aubert et al., supra. The specific activity of the iodinated hormone was 85 mCi/mg. Separation of the free iodine and iodinated hormone was done by chromatogaphy on Sephadex G-25 equilibrated with 0.1 N acetic acid.

Purification of [$^{125}$I]-$\beta_h$-EP on Sephadex G-25 in 0.1 M acetic acid gave three fractions: the first two represented radioactive $\beta_h$-EP as judged by binding tests and the third was found to be free iodine. Only the second fraction was found to be suitable for RIA studies because of the low blank value (<2%) while the first fraction gave blank value up to 25%.

EXAMPLE 2

For radioimmunoassay, approximately 7000–8000 cpm of [$^{125}$I]-$\beta_h$-EP in 0.1 ml, various quantities of unlabeled $\beta_h$-EP, or other related peptides in 0.1 ml were incubated with 0.1 ml of antiserum to $\beta_h$-EP in cold at 4° C for a period of 16–20 hr. All dilutions for radioimmunoassay were carried out in 0.01 M sodium phosphate buffer pH 7.5 containing 0.15 M NaCl, 1% bovine serum albumin and 0.33% EDTA in 12 × 75 glass tubes. Separation of the bound and free hormone was achieved by addition of 0.5 ml of phosphate buffer pH 7.5 containing 20 mg Norit and 10 mg Dextran T-70 per ml. The tubes were allowed to stand in cold for ten min. after which they were centrifuged for 30 min. in cold at 5000 rpm. 0.5 ml of the clear supernatant was mixed with 5 ml of Scintillation fluid (PCS) and counted in a Packard beta counter. The procedure for counting gamma radiation by liquid scintillation spectrophotometry was essentially that of Herscowitz and McKillip, J. Immological Methods 4; 253 (1974).

The sensitivity of the present assay for $\beta_h$-EP was seen to be in the range of 0.1–10 ng. $\beta_c$-(6-31) exhibited a parallel inhibition curve but had 40% immunoreactivity as compared with $\beta_c$-EP. On the other hand, $\beta_h$-EP-(1-5)-(16-31) showed very weak cross reaction. It may be noted that $\beta_h$-LPH, which contains the complete amino acid sequence of $\beta_h$-EP, had only 10% immunoreactivity. $\beta_c$-EP-(20-31) and met-enkephalin ($\beta_c$-EP-(1-5)) did not show any cross reactivity. Thus, residues 6-15 of $\beta_c$-EP represent the antigenic determinant of $\beta$-EP.

I claim:

1. An antigen comprising $\beta$-endorphin covalently bound to an immunogenic carrier material.

2. The antigen of claim 1 where said $\beta$-endorphin is human $\beta$-endorphin ($\beta_h$-endorphin).

3. The antigen of claim 1 wherein said $\beta$-endorphin is canoel $\beta$-endorphin ($\beta_c$-endorphin).

4. The antigen of claim 1 wherein said immogenic carrier material is human gamma globulin.

5. $^{125}$I-$\beta$-endorphin.

6. The compound of claim 5 which is $^{125}$I-$\beta_h$-endorphin.

7. An antibody having the property of specifically binding $\beta$-endorphin or fragments thereof containing the (6-15) residue sequence.

8. A radioimmunoassay for $\beta$-endorphin or a fragment thereof containing the (6-15) residue sequence which assay comprises incubating a mixture comprising the test sample containing an unknown amount of said $\beta$-endorphin or a fragment thereof containing the (6-15) residue sequence, a radiolabelled $\beta$-endorphin tracer compound and an antibody having the property of specifically binding $\beta$-endorphin or fragments thereof containing the (6-15) residue sequence; separating the free and the bound $\beta$-endorphin; counting the radioactivity from either the free or bound $\beta$-endorphin and determining the concentration of $\beta$-endorphin or fragment thereof in the test sample by reference to a standard curve.

9. The assay of claim 8 wherein said radiolabelled $\beta$-endorphin tracer compound is $^{125}$I-$\beta_h$-endorphin.

10. The assay of claim 8 wherein said incubation is carried out at 4° C. for about 16 to 20 hours.

11. The assay of claim 8 wherein said test sample comprises $\beta_h$-endorphin.

12. An immunoassay for $\beta$-endorphin or fragments thereof containing the (6-15) residue sequence which assay comprises incubating a mixture comprising the test sample containing an unknown amount of said $\beta$-endorphin or fragments thereof containing the (6-15) residue sequence, labeled $\beta$-endorphin or fragments thereof containing the (6-15) residue sequence and an antibody having the property of specifically binding $\beta$-endorphin or fragments thereof containing the (6-15) residue sequence, separating the free and the bound $\beta$-endorphin or fragments thereof containing the (6-15) residue sequence; measuring the amount of labeled $\beta$-endorphin or fragments thereof containing the (6-15) reside sequence from either the free or bound $\beta$-endorphin or fragments thereof containing the (6-15) residue sequence and determining the concentration of $\beta$-endorphin of fragments thereof containing the (6-15) residue sequence in the test sample by reference to a standard curve.

* * * * *